United States Patent
Zheng et al.

(10) Patent No.: US 8,999,403 B2
(45) Date of Patent: *Apr. 7, 2015

(54) SERISSA JAPONICA EXTRACTS AND METHODS OF USE

(71) Applicant: Avon Products, Inc., Suffern, NY (US)

(72) Inventors: Qian Zheng, Morris Plains, NJ (US); John W. Lyga, Basking Ridge, NJ (US); Uma Santhanam, Tenafly, NJ (US); Permanan Raaj Khusial, Highland Mills, NY (US); Ying Chen, Towaco, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/814,383

(22) PCT Filed: Dec. 11, 2012

(86) PCT No.: PCT/US2012/068858
§ 371 (c)(1),
(2) Date: Feb. 5, 2013

(87) PCT Pub. No.: WO2014/092682
PCT Pub. Date: Jun. 19, 2014

(65) Prior Publication Data
US 2014/0301962 A1 Oct. 9, 2014

(51) Int. Cl.
*A61K 36/74* (2006.01)
*A61K 8/97* (2006.01)
*A61Q 19/00* (2006.01)
*A61Q 19/02* (2006.01)
*A61Q 19/06* (2006.01)
*A61Q 19/08* (2006.01)

(52) U.S. Cl.
CPC . *A61K 8/97* (2013.01); *A61K 36/74* (2013.01); *A61Q 19/00* (2013.01); *A61Q 19/02* (2013.01); *A61Q 19/06* (2013.01); *A61Q 19/08* (2013.01)

(58) Field of Classification Search
USPC .......................................................... 424/725
IPC ...................................................... A61K 36/74
See application file for complete search history.

(56) References Cited

U.S. PATENT DOCUMENTS

| | | | |
|---|---|---|---|
| 6,620,798 B1 | 9/2003 | Jaffe | |
| 7,005,146 B2* | 2/2006 | Lee | 424/725 |
| 7,959,953 B2 | 6/2011 | Zimmerman et al. | |
| 8,048,456 B2 | 11/2011 | Burke-Colvin et al. | |
| 2003/0064117 A1* | 4/2003 | Hu et al. | 424/725 |
| 2012/0282194 A1 | 11/2012 | Florence et al. | |

FOREIGN PATENT DOCUMENTS

| | | | |
|---|---|---|---|
| CN | 101780179 A | * | 7/2010 |
| JP | 1056619 A | | 3/1989 |
| KR | 20000049439 A | | 8/2000 |
| KR | 2008035258 A | * | 4/2008 |
| WO | 2005/000262 A1 | | 1/2005 |

OTHER PUBLICATIONS

Lei et al. Zhongcaoyao. 1999. vol. 30, No. 5, pp. 336-339. CAPLUS Abstract enclosed.*
Australian National Data Service Australian Organism Collection. URL:<http://rda.ebi.edu.au/default.jsp?collectionId=4993>. Oct. 2012. p. 1.
G. Costin and V. Hearing, "Human skin pigmentation: melanocytes modulate skin color in response to stress," The FASEB Journal vol. 21, pp. 976-994, Apr. 2007.
Lodish, et al. Molecular Cell Biology, W.H. Freeman, New York, NY 4th edition, 2000.
Shibata et al.; Regulation of Intracellular Accumulation of Mutant Huntingtin by Beclin 1; JBC (2006) 281(20) 14474-14485.
Glick et al.; Autophagy: cellular and molecular mechanisms; J Pathol. (2010) 221(1):3-12.
Levine et al., Autophagy in aging, disease and death: the true identity of a cell death impostor; Cell Death and Differentiation (2009) 16, 1-2.
Pattison et al.; Atg7 Induces Basal Autophagy and Rescues Autophagic Deficiency in CryABR120G Cardiomyocytes; Circulation Research. 2011; 109: 151-160.
Onodera et al.; Autophagy is Required for Maintenance of Amino Acid Levels and Protein Synthesis under Nitrogen Starvation; The Journal of Biological Chemistry, 280, 31582-31586.
Proikas-Cezanne et al.; Human WIPI-1 puncta-formation: A novel assay to assess mammalian autophagy; FEBS Letters 581 (2007) 3396-3404.
Proikas-Cezanne et al.; WIPI-1a (WIPI49), a member of the novel 7-bladed WIPI protein family, is aberrantly expressed in human cancer and is linked to starvation-inducedautophagy; Oncogene (2004) 23, 9314-9325.
Ho et al; WIPI1 Coordinates Melanogenic Gene Transcription and Melanosome Formation via TORC1 Inhibition. The Journal of Biological Chemistry vol. 286, No. 14, pp. 12509-12523, Apr. 8, 2011.
Proikas-Cezanne et al.; Assessing Mammalian Autophagy by WIPI-1/Atg18 Puncta Formation; Methods Enzymol. 2009;452:247-60.
Kew Royal Botanical Garden, World checklist of selected plant families, *Serissa* Serissoides. Indication of acceptance as 2011. http://apps.kew.org/wcsp/acceptedRef.do;jsessionid=D5FD4A5E54196358A133DE3B920C5FF9?name-id=190836.
NCBI Taxonomy ID: 58678. Indication of acceptance as 2009, http://ww.ncbi.nih.gov/Taxonomy/Browswer/wwwtax.cgi?lvl=o&id=58378.
U.S. Appl. No. 13/793,109, filed Mar. 11, 2013, Zheng, Qian et al.
U.S. Appl. No. 14/066,862, filed Oct. 30, 2013, Lyga, John W. et al.
U.S. Appl. No. 14/055,037, filed Oct. 16, 2013, Khusial, Permanan Raaj.

* cited by examiner

*Primary Examiner* — Chris R Tate
(74) *Attorney, Agent, or Firm* — David M. Joyal; Joan M. McGillycuddy

(57) ABSTRACT

Methods of using extracts of *Serissa japonica* to impart benefits to skin and/or improve skin conditions resulting from aging or damaged skin.

5 Claims, 1 Drawing Sheet

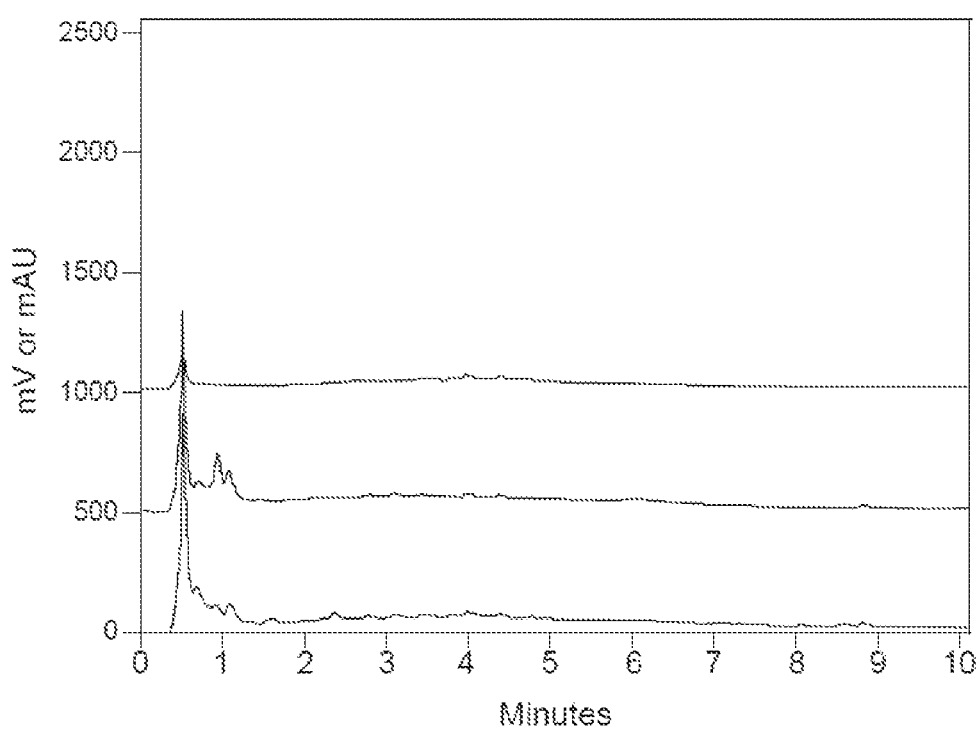

SERISSA JAPONICA EXTRACTS AND METHODS OF USE

CROSS-REFERENCE TO RELATED APPLICATIONS

This application claims priority benefit, under the national stage entry under 35 U.S.C. 371 of International Application No. PCT/US12/68858, filed on Dec. 11, 2012 the contents of which application are hereby incorporated by reference in their entirety. PCT application no. PCT/US12/68858 was filed concurrently with and claims priority to PCT Application Serial No. PCT/US12/68856 filed on Dec. 11, 2012; PCT Application Serial No. PCT/US12/68865 filed on Dec. 11, 2012; PCT Application Serial No. PCT/US12/68866 filed on Dec. 11, 2012; U.S. application Ser. No. 13/710,617 filed on Dec. 11, 2012; and U.S. application Ser. No. 13/710,585 filed on Dec. 11, 2012, the entirety of each of which is incorporated by reference herein in their entirety for all purposes.

FIELD OF INVENTION

The present invention relates generally to cosmetic compositions incorporating *Serissa japonica* extracts and their use to reduce fine lines and wrinkles, improve skin tone and lighten discolorations of the skin and to improve the overall appearance of skin by increasing epidermal thickness, reducing melanin production, and stimulating the production of collagen and/or halyuronic acid.

BACKGROUND OF THE INVENTION

Consumers are increasingly interested in cosmetics that treat, mitigate, or delay the signs of aging or aged skin. The signs of aging or aged skin manifest themselves in lines and wrinkles, sagging, dullness, discoloration, uneven tone, and/or rough texture. Further, aged skin lacks strength and elasticity and is therefore fragile. The cosmetics industry is actively pursuing products that may be used to reduce signs of aging or aged skin (anti-aging compounds) and thereby provide anti-wrinkle, rejuvenating, and skin lightening benefits.

Human skin is broadly divided into two layers: the surface epidermis which provides an anatomical barrier to foreign elements and maintains the body's internal environment, and the underlying dermis which provides nutritional and structural support to the epidermis. The epidermis mainly consists of keratinocytes and is comprised of several sub-layers (from the innermost outwards): Stratum germinativum/Stratum basale, Stratum spinosum, Stratum granulosum, and Stratum corneum. The keratinocytes, generated by the mitosis of keratinocyte stem cells, originate in the stratum basale and then push up through the strata. As these cells move to the surface of the skin they undergo gradual differentiation, becoming anucleated, flattened, and highly keratinized. During this process the keratinocytes become highly organized. They form desmosomes, cellular junctions, between each other and, through the excretion of keratin proteins and lipids, form an extracellular matrix which strengthens the skin. Eventually the keratinocytes die off and form the stratum corneum. In healthy skin, keratinocytes are shed and replaced continuously every 30 days.

While the keratinocytes are within the stratum basale they acquire melanin, a black ultraviolet light absorbing pigment, from melanocytes. Melanocytes produce melanin within organelles known as melanosomes and then transfer the melanin containing melanosomes to neighboring keratinocytes via their dendrites. Within each keratinocyte the melanosomes form a melanin cap which is retained within the keratinocyte until the keratinocyte is shed from the skin. The melanin cap reduces ultra-violet-induced DNA damage to the human epidermis and the underlying cells and tissues. Melanin provides the skin with its color and thus the intensity of skin color is directly related to the number, size, melanin content, rate at which melanin containing melanosomes are formed, rate at which the melanin containing melanosomes are transferred to keratinocytes, and rate at which melanin degrades within keratinocytes. For a more detailed background on melanin, see G. Costin and V. Hearing, "Human skin pigmentation: melanocytes modulate skin color in response to stress," The FASEB Journal Vol. 21, pages 976-994, April 2007, the disclosure of which is incorporated herein by reference in its entirety.

Hyaluronic acid (HA), a gel-like aminoglycan, also plays an important role in normal epidermis. HA is an integral part of the extracellular matrix of basal keratinocytes, maintaining the extracellular space and providing an open as well as hydrated structure for the passage of nutrients. HA also acts as a free-radical scavenger, contributing to epidermal's protection against solar radiation. HA may also act as a modulator of keratinocyte proliferation and migration.

The dermis is the underlying layer of the skin located between the epidermis and subcutaneous tissue. Since the epidermis lacks blood vessels, the cells of the epidermis rely upon the blood vessels in the dermis for their nutrients and oxygen. The dermal-epidermal junction (DEJ) is a specialized structure that maintains close contact between the lamina densa, a layer of extracellular matrix upon which the epithelium sits, and the underlying connective tissue of the dermis. The DEJ is comprised mainly of collagen and elastin and structured as interlocking finger-like projections from the epidermal and dermal layers called Rete ridges. The Rete ridges increase the surface area of the epidermis exposed to the dermis at the DEJ, so that the transfer of necessary nutrients/oxygen is more efficient, and the two layers of the skin form a strong bond that resists mechanical stress (shear). Additionally, the dermis is the thickest of the skin layers and comprises the extracellular matrix of the skin, which is maintained by fibroblast cells. Fibroblasts maintain the structural integrity of connective tissues by continuously secreting precursors of the extracellular matrix. The main structural component of the dermis is a protein called collagen. Bundles of collagen molecules pack together throughout the dermis, accounting for three-fourths of the dry weight of skin. Collagen has great tensile strength; along with soft keratin, it is responsible for skin strength and elasticity. For a more detailed background on collagen, see Lodish, et al. Molecular Cell Biology, W.H. FREEMAN, New York, N.Y. 4th edition, 2000, the disclosures of which is incorporated herein by reference in their entirety.

Histological studies of the skin show that as aging occurs, the skin undergoes structural, functional, and metabolic changes that parallel the aging and degenerative changes in other body organs. While chronological and/or hormonal aging play a significant role in skin aging, environmental stresses such as sun exposure may initiate and/or accelerate the aging of the skin due to, in part, oxidative damage from overexposure to ultraviolet (UV) sunlight. In aged and/or aging skin the cells may take longer to replenish, be less numerous, and/or breakdown more quickly. In particular, as aging occurs, the production of collagen is reduced while the degradation is accelerated due to an overproduction of collagenase, i.e. a protease that breaks down collagen. The resulting collagen deficiency may lead to reduction in skin strength and elasticity. Further, given that collagen is a major component of the DEJ, the DEJ flattens out with aging, such that the skin is more fragile and more likely to shear. As the DEJ flattens the amount of nutrients/oxygen transferred to the epidermis through the DEJ is reduced because the surface area in contact with the epidermis shrinks. The reduction of HA within the epidermal extracellular matrix reduces the epidermis's ability to transfer the available nutrients/oxygen to its cells. This inefficient nutrient/oxygen transport impacts the keratinocytes and melanocytes of the epidermis. The keratinocytes renewal rate is reduced and as a consequence the stratum corneum loses its capacity to retain moisture and the skin dehydrates. Moreover, the melanocytes become less numerous and the remaining melanocytes may produce a greater amount of melanin leading to discoloration/hyperpigmentation of the skin and/or solar lentigenes, "age spots." At the surface of the skin, aged or aging skin may exhibit lines and wrinkles, sagging, dullness, discoloration, uneven tone, rough texture, and the like. Additionally, aged or aging skin exhibits less strength and flexibility and is more fragile. These signs of aging may be exacerbated by common medications such as those prescribed for the treatment of Parkinson's disease, i.e. Levodopa, or menopause, i.e. hormone therapies.

One well known product used for anti-aging skin care is retinol which has proven to be effective in diminishing the visual signs of aging on facial skin. Retinol has negative effects including the tendency to cause skin irritation or the tendency to breakdown when exposed to oxygen or UV thereby impairing its effectiveness.

*Serissa japonica*, also known as the tree of a thousand stars, is an evergreen shrub with small, bright green, oval leaves that is native to open sub-tropical woodlands and wet meadows in southeast Asia. Depending on the variety, small white or pink flowers cover the tree in late spring. The natural color of the trunk is gray and the bark roughens with age.

There remains a need for cosmetic compositions which address the signs of aging, in particular the appearance of wrinkles, lines, and discolored areas. It is therefore an object of the present invention to provide new compositions and methods for treating, ameliorating, and/or preventing signs of aged or aging skin. It is a further object of the invention to improve the overall appearance of aging or aged skin.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has been found that extracts of *Serissa japonica* are surprisingly potent regulators of collagen, hyaluronic acid, and melanin synthesis within the body and thus are beneficial agents against signs of aging and discoloration within the skin.

One embodiment of the current invention relates to a topical composition including a *Serissa Japonica* plant extract; and a cosmetically, dermatologically, pharmaceutically, or physiologically acceptable vehicle. In a further embodiment, the plant extract may be from the leaves and stems of *Serissa Japonica*. In certain embodiments, the composition may be an aerosol spray, cream, emulsion, solid, liquid, dispersion, foam, gel, lotion, mousse, ointment, powder, patch, pomade, solution, pump spray, stick or towelette.

In another embodiment, the plant extract may be present in the composition in an amount sufficient to increase collagen and hyaluronic acid proliferation, increase epidermal thickness, reduce melanin synthesis; or any combination thereof. In one embodiment, the plant extract may be present in an amount from about 0.0001 wt % to about 90 wt %, based on the total weight of the composition, and in a further embodiment, the plant extract may be present in an amount from about 0.01 wt % to about 10 wt %, based on the total weight of the composition. In certain embodiments, the plant extract may be in an amount sufficient to alleviate the aesthetic appearance of wrinkles, pigment spots, skin sagging, loss of skin elasticity, mottled skin appearance or any combination thereof.

A further embodiment of the current invention relates to a method of improving the aesthetic appearance of an aging skin in need thereof, by topically applying to the skin the above-noted composition in an amount effective to improve the aesthetic appearance of skin. In one embodiment, the skin is sensitive skin. In a further embodiment of the invention, the composition is topically applied to the skin at least once daily for at least one week.

In certain embodiments the aging may be due to chronological, hormonal, or environmental effects. In further embodiments, the improvement in aesthetic appearance is selected from the group of: (a) treatment, reduction, and/or prevention of fine lines or wrinkles; (b) reduction of skin pore size; (c) improvement in skin thickness, plumpness, and/or tautness; (d) improvement in skin suppleness and/or softness; (e) improvement in skin tone, radiance, and/or clarity; (f) improvement in procollagen and/or collagen production; (g) improvement in maintenance and remodeling of elastin; (h) improvement in skin texture and/or promotion of re-texturization; (i) improvement in skin barrier repair and/or function; (j) improvement in appearance of skin contours; (k) restoration of skin luster and/or brightness; (l) replenishment of essential nutrients and/or constituents in the skin; (m) improvement of skin appearance decreased by aging and/or menopause; (n) improvement in skin moisturization and/or hydration; (o) increase in and/or preventing loss of skin elasticity and/or resiliency; (p) treatment, reduction, and/or prevention of skin sagging; (q) treatment, reduction, and/or prevention of discoloration of skin; and (r) any combination thereof. In other embodiments of the current invention the improvement of the skin may be due to an increase in collagen synthesis, an increase in hyaluronic acid synthesis, an increase epidermal thickness, a reduction in melanin synthesis; or any combination thereof.

In yet another embodiment of the invention, the extract may be present in an amount about 0.0001 wt % to about 90 wt % based on the total weight of the composition, and in a further embodiment may be present in an amount of from about 0.01 wt % to about 10 wt % of the total weight of the composition. In certain embodiments, the *Serissa Japonica* plant extract may be derived from the leaves and stems of the *Serissa Japonica* plant.

Another embodiment of the current invention is directed to a method of improving the barrier function and viability of the skin by topically applying to the skin the above-noted composition in an amount effective to increase collagen synthesis, to increase hyaluronic acid synthesis, increase epidermal thickness, reduce melanin synthesis, or any combination thereof. In a certain embodiment of this method the extract is derived from leaves and stems of *Serissa Japonica*. In further embodiments of the method, the plant extract is present in an amount of about 0.0001 wt % to about 90 wt % based on the total weight of the composition, and in still further embodiments, the plant extract is present in an amount of about 0.01 wt % to about 10 wt % based on the total weight of the composition.

A further embodiment of the current method is directed to treating wrinkles, fine lines, or a sagging skin, by topically applying to the skin the above-noted composition in an amount effective to treat the skin in need thereof.

A method for lightening skin in need thereof is another embodiment of the current invention. The method involves topically applying to skin in need of lightening the above-noted composition in an amount effective to achieve a lightening benefit. In additional embodiments of this method the plant extract is present in an amount of about 0.01 wt % to about 10 wt % based on the total weight of the composition.

In certain embodiments the lightening benefit may be selected from the group consisting of: (a) bleaching hyper-pigmented hair, skin, lips and/or nails; (b) reducing age spots; (c) evening or optimizing skin discoloration; (d) improving the appearance of dark circles under the eyes; (e) treating melasma, cholasma, freckles, after-burn scars, and post-injury hyper-pigmentation; (f) bleaching hair on the scalp, legs, face, and other areas where bleaching and color reduction are desired; (g) bleaching nail stains; and (h) combinations thereof. The lightening benefit may be due to a reduction in melanin synthesis, and in certain embodiments the reduction of melanin synthesis may be about 20-100%.

A further embodiment of the current invention is directed to a method of treating skin comprising topically applying to an area of the skin in need thereof an effective amount of a *Serissa japonica* extract that modulates a skin biomarker, wherein the ability of the *Serissa japonica* extract to modulate a skin biomarker has been determined by an assay which measures the amount of change in a skin biomarker selected from the group comprising epidermal thickening; total collagen; pro-collagen; and hyaluronic acid binding protein in skin cells and/or skin cell pre-differentiation precursors that have been contacted with the *Serissa japonica* extract.

These and other aspects of the present invention will be better understood by reference to the following detailed description and accompanying figures.

BRIEF DESCRIPTION OF THE DRAWINGS

FIG. 1 is a HPLC profile of an extract of *Serissa japonica*.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, and some features may be exaggerated to show details of one embodiment components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

The successful restoration of youthful skin must address a variety of key issues including: vitality of fibroblasts and keratinocytes, cell-cell adhesion in the epidermis and dermis, cell nourishment to the epidermis, cell-cell anchoring and adhesion between keratinocytes, communication between the dermis and epidermis, collagenase overproduction, collagen replacement, and mechanical properties of the skin. The present invention addresses these key issues through the use of cosmetic compositions incorporating extracts of *Serissa japonica*. In particular, the compositions of the current invention are used to reduce fine lines and wrinkles, improve skin tone and reduce discoloration and to improve the overall appearance of skin. The extracts of *Serissa japonica* increase epidermal thickness, reduce melanin production, stimulate the production of collagen and/or hyaluronic acid, and/or some combination thereof.

The present invention provides compositions for topical application which comprise an effective amount of an extract of *Serissa japonica* to treat, reverse, ameliorate and/or prevent signs of skin damage or skin aging. Such benefits include without limitation, the following:

(a) treatment, reduction, and/or prevention of fine lines or wrinkles, (b) reduction of skin pore size, (c) improvement in skin thickness, plumpness, and/or tautness;

(d) improvement in skin suppleness and/or softness;

(e) improvement in skin tone, radiance, and/or clarity;

(f) improvement in procollagen and/or collagen production;

(g) improvement in maintenance and remodeling of elastin;

(h) improvement in skin texture and/or promotion of re-texturization;

(i) improvement in skin barrier repair and/or function;

(j) improvement in appearance of skin contours;

(k) restoration of skin luster and/or brightness;

(l) replenishment of essential nutrients and/or constituents in the skin;

(m) improvement of skin appearance decreased by aging and/or menopause;

(n) improvement in skin moisturization and/or hydration;

(o) increase in and/or preventing loss of skin elasticity and/or resiliency;

(p) treatment, reduction, and/or prevention of skin sagging; and/or (q) treatment, reduction, and/or prevention of discoloration of skin.

In practice, the compositions of the invention are applied to skin in need of treatment. That is, skin which suffers from a deficiency or loss in any of the foregoing attributes or which would otherwise benefit from improvement in any of the foregoing skin attributes.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, sec. 201(i).

In one embodiment, compositions incorporating *Serissa japonica* extracts are used to lighten, i.e. reduce the pigmentation, of hair, skin, lips, and/or nails to achieve the following lightening benefits:

(a) bleaching hyper-pigmented hair, skin, lips and/or nails;

(b) reducing age spots;

(c) evening or optimizing skin discoloration;

(d) improving the appearance of dark circles under the eyes;

(e) treating melasma, cholasma, freckles, after-burn scars, and post-injury hyper-pigmentation;

(f) bleaching hair on the scalp, legs, face, and other areas where bleaching and color reduction are desired; and/or (e) bleaching nail stains.

In practice, the compositions of the invention are applied to skin in need of treatment. That is, skin which suffers from a deficiency or loss in any of the foregoing attributes or which would otherwise benefit from improvement in any of the foregoing skin attributes.

DEFINITIONS

All terms used herein are intended to have their ordinary meaning unless otherwise provided.

The term "active amount" refers to the amount of *Serissa japonica* extract absent diluent, solvent, carrier, filler or any other ingredient. An "amount effective" or an "effective amount" to provide a particular anti-aging benefit to the skin refers to the "active amount" of extract required to provide a clinically measurable improvement in the particular manifestation of aging, i.e., an unwanted feature associated with aging, when applied or administered for a time sufficient to provide a clinically measurable improvement in the particular manifestation of aging.

As used herein, the term "a person in need thereof" refers to an individual with a normal but noticeable and undesired skin condition, unwanted feature, due to aging, e.g. lines and wrinkles, sagging, dullness, discoloration, uneven tone, rough texture, etc., or an individual that elects to decrease the effects of aging in the absence of a noticeable and undesired skin condition, i.e. as a preventative or prophylactic.

As used herein, the term "consisting essentially of" is intended to limit the invention to the specified materials or steps and those that do not materially affect the basic and novel characteristics of the claimed invention, as understood from a reading of this specification.

By "cosmetically acceptable" it is meant that a particular component is generally regarded as safe and nontoxic at the levels employed.

As used herein, the term "discoloration" includes discrete pigmentation and mottled pigmentation. Discrete pigmentation are distinct uniform areas of darker pigment and may appear as brown spots or freckles on the skin and may include solar lentigo, darkened spots on the skin caused by aging and the sun also known as "liver spots," "senile freckles," or "age spots," or ephelis, freckles. Mottled pigmentation are dark blotches that are larger and more irregular in size and shape than discrete pigmentation and may include conditions such as chloasma, melasma, skin discolorations caused by hormones, i.e. as the result of pregnancy, birth control pills, or estrogen replacement therapy. The discoloration may be the result of external factors including, but not limited to, UV-R, tanning and photoaging, drugs, and/or chemicals, or internal factors including, but not limited to, genetics, hormonal influences, and/or inflammation.

Elasticity of the skin refers to the springiness and resilience of skin's ability to regain its original shape and size after deformation. Elasticity of the skin may be evaluated by a pinch test that can either cause deformation by stretching or squeezing the skin.

As used herein, the term "essential oil" refers to the volatile ethereal fraction obtained from a plant or plant part by a physical separation process such as distillation or chromatographic separation. The essential oils are typically terpenoids often comprising monoterpenes and have the odor and flavor of the plant from which they were extracted.

The term "lightening" is meant herein to refer to any detectable reduction in skin color/pigmentation, of hair, skin, lips, and/or nails, e.g., a reduction visible to the naked eye, that occurs after contacting the skin of an individual with a treatment regimen comprising a *Serissa japonica* extract. As an example, this may refer to a evening or optimization of a discoloration of the skin, i.e. bleaching age spots, freckles, etc. to reduce or eliminate the color difference between the discoloration and the surrounding skin; and/or an overall lightening of the individual's normal pigmentation/skin color, i.e. skin lightening. The terms reducing pigmentation, lightening, bleaching, or color reduction are used interchangeably herein. Without wishing to be bound to a particular theory, applicants believe that the current herbal extracts achieve this lightening effect by impairing the synthesis of melanin thereby reducing melanin production. The term "reducing melanin production" is used herein to mean a detectable lowering of the amount of melanin synthesized by melanocytes exposed to a *Serissa japonica* extract as compared to the amount of melanin synthesized in the absence of such an inhibiting compound. The term "reduction" as used herein in relation to melanin means the complete prevention, control of secretion, or a degree of reduction of the formation of melanin, respectively. The term "lowering" in one embodiment refers to about a 10% to about a 100% decrease in the amount of melanin thereby synthesized. More in one embodiment, the term "lowering" refers to about a 25% to about a 100% decrease in the amount of melanin synthesized. Still more in one embodiment, the term "lowering" refers to about a 35% to about 100% decrease in the amount of melanin synthesized. The terms lowering, reducing, decreasing, suppressing and inhibiting, when used in relation to melanin production, are intended to be used interchangeably. Such reduction in melanin production may be evaluated subjectively or by using assays including, but not limited to, in vitro, ex vivo, animal models, and/or clinical models known to those skilled in the art. For example, the reduction of melanin synthesis may be established using methods known to those skilled in the art including, but not limited to, human melanocyte cultures, mouse melanoma cultures, see Example 3 below and U.S. Pat. No. 7,189,419 hereby incorporated by reference in its entirety for all purposes, HRM2 hairless mouse model, see Chung, et al., "Evaluation of in vitro and in vivo anti-melanogenic activity of a newly synthesized strong tyrosinase inhibitor (E)-3-(2,4 dihydroxybenzylidene)pyrrolidine-2,5-dione (3-DBP)," Biochim Biophys Acta. 2012 July; 1820(7):962-9 hereby incorporated by reference in its entirety for all purposes, Zebra fish models, See Choi, T. Y.; Kim, J. H.; Ko, D. H.; Kim, C. H.; Hwang, J. S.; Ahn, S.; Kim, S. Y.; Kim, C. D.; Lee, J. H.; Yoon, T. J. Zebrafish as a new model for phenotype-based screening of melanogenic regulatory compounds. *Pigment Cell Res.* 2007, 20, 120-127, hereby incorporated by reference in its entirety for all purposes, and MelanoDerm™ Skin Model (MatTek Corporation, Ashland, Mass.).

"Prevention" as used herein, as well as related terms such as "prevent" or "preventing," refer to affording skin not yet affected by the condition a benefit that serves to avoid, delay, forestall, minimize, or reduce the recurrence/onset of one or more unwanted features associated with the skin condition to be prevented. Such preventative benefits include, for example, delaying development and/or recurrence of the condition, or reducing the duration, severity, or intensity of one or more unwanted features associated with the condition if it eventually develops. Use of the term "prevention" is not meant to imply that all subjects in a subject population administered the cosmetic composition will never be affected by or develop the cosmetic or dermatologic conditions, damage, effect, or symptom, but rather that the subject population will exhibit a reduction in the cosmetic or dermatologic damages, effects, or symptoms. For example, many flu vaccines are not 100% effective at preventing flu in those administered the vaccine. Preventing aging refers to affording not yet affected skin a benefit that serves to avoid, delay, forestall, or minimize one or more unwanted features associated with aging, such as reducing the extent of lines and wrinkles, sagging, dullness, discoloration, uneven tone, rough texture, and/or fragileness that eventually develops at the treated area.

The term "skin" as used herein includes the skin on or in the face, mouth, neck, chest, back, arms, hands, legs, and scalp. "Thin skin" is intended to include skin that is thinned due to chronological aging, menopause, or photo-damage.

"Treatment" as used herein, as well as related terms such as "treat" or "treating," refers to eradicating, reducing, ameliorating, or reversing one or more of the unwanted features associated with the skin condition being treated, such that the consumer perceives an improvement in the appearance of the skin or other treatment benefit with respect to the condition. Treating skin aging or damage refers to eradicating, reducing, ameliorating, or reversing one or more of the unwanted features associated with aging. Unwanted features associated with aging skin, e.g., lines and wrinkles, sagging, dullness, uneven tone, rough texture, discoloration, etc. Unwanted features associated with discoloration, e.g., age spots, freckles, melasma, chloasma, post-inflammatory hyperpigmentation, etc. Treatment benefits include, e.g., reducing the appearance of lines, wrinkles, and/or sagging, restoring lustre to the skin, evening the tone of skin, softening the skin texture, and/or lightening discolorations. The present compositions and methods are suitable for use in treating dermatological conditions of the skin in numerous areas of the body, including, without limitation the face, forehead, lips neck, arms hands, legs, knees, feet chest, back, groin, buttocks, and the like. In a in one embodiment, the compositions are applied to the face.

The term "wrinkle" or "wrinkling" refers to both fine wrinkling and coarse wrinkling. Fine wrinkling or fine lines refers to superficial lines and wrinkles on the skin surface. Coarse wrinkling refers to deep furrows, particularly deep lines/wrinkles on the face and around the eyes, including expression lines such as frown lines and wrinkles, forehead lines and wrinkles, crow's feet lines and wrinkles, nasolabial fold and marionette lines and wrinkles. Forehead lines and wrinkles refer to superficial lines and/or deep furrows on skin of the forehead. Crow's feet lines and wrinkles refer to superficial lines and/or deep furrows on skin around the eye area. Marionette lines and wrinkles refer to superficial lines and/or deep furrows on skin around the mouth. Wrinkles can be assessed for number, length, and depth of the lines.

All percentages are by weight based on the total weight of the composition, unless otherwise indicated.

Cosmetic Compositions

The cosmetic compositions used in the method of the current invention comprise a botanical component derived from the *Serissa japonica* plant. *Serissa japonica* plant may be in any form including, but not limited to, the whole plant, a dried plant, a ground plant or parts thereof, including but not limited to, seeds, needles, leaves, roots, bark, cones, stems, rhizomes, callus cells, protoplasts, organs and organ systems, and meristems, an extract, a dried extract, a synthetic extract, or components and/or constituents found in, or isolated from, the plant, and/or portions of the plant, or extracts derived either directly or synthetically from the plant, or any combinations thereof. For the cosmetic compositions used in this invention the botanical component is in one embodiment derived directly from the *Serissa japonica* plants. The botanical component may be in a pure form, a semi-pure form, or unpurified form. The *Serissa japonica* botanical component may be in the form of a liquid, a semi-solid, or a solid consistency. In one embodiment, the botanical component may be an essential oil.

In one embodiment, the raw materials are collected from the leaves and stems of the *Serissa japonica* plants. In certain embodiments, the raw materials collected from the *Serissa japonica* plants are ground to small particle sizes. In addition, the raw materials may be dried to reduce water content. The raw materials may be air-dried, oven-dried, rotary evaporated under vacuum, lyophilized, or dried by any other suitable method known in the art.

The extract of *Serissa japonica* may be obtained by distilling the raw materials with a stripping agent. The stripping agent may be a liquid that is miscible, immiscible, or partially miscible with the desired extract from *Serissa japonica*. Suitable stripping agents include, but are not limited to the following: water; alcohols (such as methanol, ethanol, propanol, butanol and the like); glycols; ethers (such as diethyl ether, dipropyl ether, and the like); esters (such as butyl acetate, ethyl acetate, and the like); ketones (such as acetone, ethyl methyl ketone, and the like); dimethyl sulfoxide; acetonitrile; other organic solvents; and combinations thereof. In one embodiment, the stripping agent is immiscible with the desired extract from *Serissa japonica*. The *Serissa japonica* extract may be collected by phase separation from the stripping agent. It is believed that the stripping agent increases the overall vapor pressure of a distillation system for obtaining an extract of *Serissa japonica* and thereby reduces the boiling point of the desired product, the *Serissa japonica* extract.

In other embodiments, *Serissa japonica* botanical component may be in the form of an extract obtained by solvent extraction, in one embodiment obtained by an organic solvent extraction. Briefly, the organic solvent extraction method involves washing and extracting the raw materials, which may be whole or ground into small particle sizes, using an organic solvent. Non-limiting examples of organic solvents include methanol, ethanol, isopropanol, dichloromethane, chloroform, hexane, xylene, and petroleum ether. An extracting machine may be used for organic solvent extraction as is well known in the field. The raw materials are pushed slowly into the extracting machine by a thruster. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time suitable to extract the *Serissa japonica* plant constituents is used, typically between about 1-10 hours, more in one embodiment between about 2-8 hours, and most in one embodiment between about 3-6 hours. The temperature of extraction is between about 30° C.-100° C., in one embodiment between about 40° C.-70° C., and more in one embodiment between about 50° C.-60° C. The collected extract is then fine-filtered to remove debris, and may be used directly, or is concentrated, for example by distilling the solvent or by other conventional processing. The solution of extract actives may be rotary evaporated under vacuum or lyophilized. A typical extract's actives content is above about 25%, in one embodiment above 50%, and the extract can also be provided as an essential oil or a concentrate having a semi-solid or solid consistency.

Similarly, aqueous-organic solvent extraction involves initially collecting raw materials from the *Serissa japonica* plants, which may be whole or ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, in concentrated or dried form. Alternatively, an organic solvent may then be added to the neutralized solution to transfer the extract from an aqueous phase to an organic phase. Examples of such organic solvents include, but are not limited to, ethanol, isopropanol, butanol, pentanol, hexanol, and xylene. The extract comprising the transferred extract actives dissolved in organic solvent may be used directly as an essential oil or a concentrate, or dried by a number of different means, such as, for example, air-drying, oven-drying, rotary evaporating under vacuum or lyophilizing to a semi-solid or solid consistency.

It should also be noted that different plants containing different constituents can be mixed and extracted together with *Serissa japonica*. This process of mixed extraction can in one embodiment be used for extracting those plants containing constituents with similar solubility as *Serissa japonica* in the solvent used for extraction, such as ethanol. The mixture of extracts can be concentrated and stored in an appropriate solvent.

In another embodiment, the *Serissa japonica* extract as used herein, also includes "synthetic" extracts, i.e., various combinations of known *Serissa japonica* plant components and/or constituents that are combined to substantially mimic the composition and/or activity of a *Serissa japonica* plant extract of natural origin. In one embodiment, the synthetic extracts have substantially the same number of active components as a natural *Serissa japonica* plant material. The correspondence of the numerical incidence of actives between the synthetic extracts and the natural *Serissa japonica* plant material may also be described in terms of "percent commonality." The synthetic extract has about 50 percent or more commonality to the chemical composition of a plant or natural extract. In other words, the synthetic extract has about 50 percent or more of the active ingredients found in the plant or a natural extract. More in one embodiment, the chemical composition of the synthetic extract has about 70 percent or more commonality to the chemical composition of a plant or a natural extract. Optimally, a synthetic extract has about 90 percent or more commonality to the chemical composition of a plant or a natural extract.

The compositions according to the invention can be formulated in a variety of forms for topical application and will comprise from about 0.0001% to about 90% by weight of an extract of *Serissa japonica*, and in one embodiment will comprise from about 0.0005% to about 25% by weight, and more in one embodiment from about 0.001% to about 10% by weight. Within the more in one embodiment range, the composition may comprise a *Serissa japonica* extract within a range from about 0.005%, 0.01%, 0.05%, 0.1%, 0.25%, 0.5%, 0.75% or 1% up to 5%, 7.5% or 10% by weight of the total composition. The compositions will comprise an effective amount of an extract of *Serissa japonica*, by which is meant an amount sufficient to reduce and/or inhibit the appearance of signs of aging or damage in a given area of skin when topically applied thereto. The above amounts refer to an "active amount" of a *Serissa japonica* extract.

In accordance with the invention, compositions comprising components from the *Serissa japonica* plant include, but are not limited to, topically applied formulations, anti-oxidants, anti-inflammatories, sunscreens, cosmetics (including makeup), personal care products (e.g., antiperspirants or deodorants for controlling body odor), topicals, skin penetration enhancers, and the like. Also in accordance with this invention, the *Serissa japonica* plant components and additional ingredients comprising such compositions may be formulated in a variety of product forms. The compositions may be prepared in targeted delivery systems, e.g. creams, lotions, gels, toners, serums, transdermal patches, and the like, particularly for topical administration. Targeted delivery and/or penetration enhancement may also be achieved by iontophoresis.

The present invention further provides the compositions comprising the *Serissa japonica* plant components for the current method be in one embodiment topically administered for targeted delivery. The method of the current invention is suitable for all skin types, such as sensitive, normal, oily, or combination. In particular embodiments, the compositions may be in one embodiment applied to sensitive skin or hair types. The compositions are applied to the skin or hair for a period of time sufficient to improve the aesthetic appearance of conditions related to skin, including unwanted features associated with aging, e.g., lines and wrinkles, sagging, dullness, uneven tone, rough texture, discoloration, etc. The compositions may be applied topically once, twice, or more daily, in one embodiment once a day. The daily application may be applied for a period of one week, two weeks, four weeks, or more.

The compositions may be formulated into liposomes which can comprise other additives or substances, and/or which can be modified to more specifically reach or remain at a site following administration. The compositions of the present invention yield improvements to the aesthetic appearance by treating at least one of the unwanted features related to skin aging or damage.

Another embodiment of the method of the current invention encompasses compositions comprising a cosmetically or dermatologically acceptable formulation which is suitable for contact with living animal tissue, including human tissue, with virtually no adverse physiological effect to the user. Compositions embraced by this invention can be provided in any cosmetically and/or dermatologically suitable form, in one embodiment as a lotion or cream, but also in an anhydrous or aqueous base, as well as in a sprayable liquid form. Other suitable cosmetic product forms for the compositions used in this invention include, for example, an emulsion, a cream, a balm, a gloss, a lotion, a mask, a serum, a toner, an ointment, a mousse, a patch, a pomade, a solution, a spray, a wax-based stick, or a towelette. In addition, the compositions can include one or more compatible cosmetically acceptable adjuvants commonly used and known by the skilled practitioner, such as colorants, fragrances, emollients, humectants, preservatives, vitamins, chelators, thickeners, perilla oil or perilla seed oil (WO 01/66067 to a "Method of Treating a Skin Condition," incorporated herewith in its entirety for all purposes) and the like, as well as other botanicals such as aloe, chamomile, and the like, and as further described below.

Also, embraced by the invention are transdermal modes of delivery, such as patches and the like, with or without a suitable penetration enhancer. The methods and compositions embodied by the invention provide a means by which the *Serissa japonica* components can be effectively administered in a transdermal system. Accordingly, a transdermal means of delivering a composition or formulation (often with a penetration enhancing composition) to the skin is that of the transdermal patch or a similar device as known and described in the art. Transdermal patches are designed to deliver an effective amount of compound across a user's skin. Transdermal patches typically involve a liquid, gel, solid matrix, or pressure-sensitive adhesive carrier into which the *Serissa japonica* extract may be incorporated. Patch formulations and preparations are well known in the art. See for example "Dermatological and Transdermal Formulations" (Drugs and the Pharmaceutical Sciences, Vol 119) by Kenneth A Walters (Editor), Marcel Dekker and "Transdermal Drug Delivery" (Drugs & the Pharmaceutical Sciences) by Richard H. Guy (Editor), Jonathan Hadgraft (Editor) 2nd Rev & ex edition Marcel Dekker and "Mechanisms of Transdermal Drug Delivery" (Drugs & the Pharmaceutical Sciences, Vol 83) edited by Russell O. Potts and Richard H. Guy (1997). Examples of such devices are disclosed in U.S. Pat. Nos. 5,146,846; 5,223,262; 4,820,724; 4,379,454; and 4,956,171; and U.S. Patent Publication No. US20110300198, all of which are incorporated herein by reference in their entirety and such descriptions are not meant to be limiting. The transdermal mode of storing and delivering the compositions onto the skin, including hair, and forming the active composition is convenient and well-suited for the purposes of an embodiment of the present invention. In a in one embodiment method, the application occurs through a sustained release vehicle, carrier, or diluent, e.g., a topically applied sustained released patch. In one embodiment, when a topical patch is used, the patch is applied to the desired area for extended period of time. In one embodiment, the extended period of time is greater than one hour, most in one embodiment the extended period of time is overnight, i.e., when the user is sleeping. Additionally, the transdermal patches may be formulated to provide extended benefits for a period of about 1-7 days, in one embodiment, about 2 to 7 days, and more in one embodiment about 3-7 days. Such extended wear patches may be particularly well suited to treat, ameliorate, and/or prevent discoloration. Further, given that many compounds that lighten skin pigmentation/color are UV sensitive the transdermal patch may be used to permit continued treatment while wearer is exposed to sunlight thereby providing the wearer with greater freedom. In such instances, the exterior of the transdermal patch is in one embodiment flesh colored, and more in one embodiment the patch should closely match the skin color of the wearer to provide discreet treatment.

The topical compositions can include one or more cosmetically acceptable vehicles. Such vehicles may take the form of any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, in one embodiment organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The oil phase of the emulsion in one embodiment has one or more organic compounds, including emollients; humectants (such as butylene glycol, propylene glycol, Methyl gluceth-20, and glycerin); other water-dispersible or water-soluble components including thickeners such as veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms, more in one embodiment 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl®) are also suitable. Examples of in one embodiment volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Non-limiting emulsifiers include emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. The in one embodiment emulsifiers include soya sterol, cetyl alcohol, stearic acid, emulsifying wax, acrylates, silicone containing emulsifiers and mixtures thereof. Other specific emulsifiers that can be used in the composition of the present invention include, but are not limited to, one or more of the following: $C_{10-30}$ alkyl acrylate crosspolymer; Dimethicone PEG-7 isostearate, acrylamide copolymer; mineral oil; sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11$^{th}$ Edition 2006, the disclosure of which is hereby incorporated by reference.

These emulsifiers typically will be present in the composition in an amount from about 0.001% to about 10% by weight, in particular in an amount from about 0.01% to about 5% by weight, and more in one embodiment, from about 0.1% to about 3% by weight.

The oil phase may comprise one or more volatile and/or non-volatile silicone oils. Volatile silicones include cyclic and linear volatile dimethylsiloxane silicones. In one embodiment, the volatile silicones may include cyclodimethicones, including tetramer ($D_4$), pentamer ($D_5$), and hexamer ($D_6$) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are in one embodiment non-volatile silicone oils. The non-volatile silicone oils will typically have a viscosity from about 10 to about 60,000 centistokes at 25° C., in one embodiment between about 10 and about 10,000 centistokes, and more in one embodiment still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted with various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -(EO)m- and/or -(PO)n- groups, where EO is ethyleneoxy and PO is 1,2-propyleneoxy, the side chains being typically capped or terminated with hydrogen or lower alkyl groups (e.g., C1-6, typically C1-3). Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. In one embodiment examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate.

The water-in-silicone emulsifiers typically will be present in the composition in an amount from about 0.001% to about 10% by weight, in particular in an amount from about 0.01% to about 5% by weight, and more in one embodiment, below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil-containing phase will typically comprise from about 10% to about 99%, in one embodiment from about 20% to about 85%, and more in one embodiment from about 30% to about 70% by weight, based on the total weight of the emulsion, and the aqueous phase will typically comprise from about 1% to about 90%, in one embodiment from about 5% to about 70%, and more in one embodiment from about 20% to about 60% by weight of the total emulsion. The aqueous phase will typically comprise from about 25% to about 100%, more typically from about 50% to about 95% by weight water.

The compositions may include liposomes. The liposomes may comprise other additives or substances and/or may be modified to more specifically reach or remain at a site following administration.

The daily doses recommended in conformity with the invention range from 0.5 to 2600 mg/day, and in one embodiment from 5 to 1200 mg/day of *Serissa japonica* extract. The compositions of the invention can be taken for several days, weeks or months. The regimen of treatment can be repeated many times in a year and can even be continuous.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives (e.g., DMDM Hydantoin/Iodopropynylbutylcarbonate), stabilizers, pharmaceutical agents, photostabilizing agents, neutralizers (e.g., triethanolamine) and mixtures thereof. In addition to the foregoing, the cosmetic compositions of the invention may contain any other compound for the treatment of skin disorders.

The composition may comprise additional active ingredients having anti-aging benefits, as it is contemplated that synergistic improvements may be obtained with such combinations. Exemplary anti-aging components include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.); estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

The present compositions may also include skin whiteners. Some examples of such suitable skin whiteners include, but are not limited to, one or more of the following: ascorbyl glucoside, vitamin C, retinol and/or its derivatives, arbutin, bearberry extract, *rumex crispus* extract, milk proteins including hydrolyzed milk proteins, N,N,S-tris(carboxymethyl)cysteamine, oleanolic acids, perilla oil, placenta extract, *Saxifragia sarmentosa*, perilla extract, juniperic acid, TDPA, *Ligusticum chiangxiong* hart., *Asmunda japonica* thunb., *Stellaria medica* (L.) cyr., *Sedum sarmentosum* bunge, *Ligusticum lucidum* Ait., *ilex purpurea* hassk, emblica, apigenin, ascorbyl palmitol, carruba polyphenols, hesperitin, inabata polyphenol, isoliquirtigenin, kaempherol-7-neohesperidose, L-mimosine, luteolin, oil-soluble licorice extract P-T(40), oxa acid, phenyl isothiocyanate, cococin, silymarin, T4CA, teterahydro curcumin, unitrienol, ursolic-oleanolic acid, UVA/URSI, hydroquinone, kojic acid, *Glycyrrhiza glabra, Chiarella vulgaris* extract, coconut fruit extract, *Butea frondosa, Naringi crenulata, Stenoloma chusana, Azadirachta indicia, Morinda citrifolia*, or any combinations thereof, see U.S. Pat. No. 7,189,419 hereby incorporated by reference in its entirety.

Suitable hydroxyl acids include, for example, glycolic acid, lactic acid, malic acid, tartaric acid, citric acid, 2-hydroxyalkanoic acid, mandelic acid, salicylic acid, and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid, and 2-hydroxy-3-methylbenzoic acid or alkoxy derivatives thereof, such as 2-hydroxy-3-methoxybenzoic acid.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin texture (smoothness) and reducing the appearance of fine lines and coarse wrinkles. Examples include isopropyl myristate, petrolatum, isopropyl lanolate, silicones (e.g., methicone, dimethicone), oils, mineral oils, fatty acid esters, cetyl ethylhexanoate, $C_{12-15}$ alkyl benzoate, isopropyl isostearate, diisopropyl dimer dillinoeate, or any mixtures thereof. The emollient may be in one embodiment present from about 0.1 wt % to about 50 wt % of the total weight of the composition.

A skin plumper serves as a collagen enhancer to the skin. An example of a suitable and in one embodiment skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. In one embodiment sunscreens are those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A in one embodiment exfoliating agent is glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant in one embodiment from about 0.001 wt % to about 10 wt %, and more in one embodiment from about 0.01 wt % to about 5 wt %, of the total weight of the composition.

In some embodiments, additional actives may include a collagen stimulator and/or an elastin stimulator, e.g., a substance that stimulates elastin production, and/or a glycosaminoglycan enhancer. Examples of collagen, elastin, and glycosaminoglycan enhancers include, e.g., fennel extract, carrot extract, and alfalfa extract. In some embodiments the additional actives may include a collagenase inhibitor and/or elastase inhibitor. In some embodiments the invention relates to synergistic action of one or more compositions described herein with perilla oil, e.g., to provide enhanced anti-cellulite benefits to skin.

In some embodiments the cosmetic compositions can further comprise at least one collagen and/or elastin stimulator. Such collagen or elastin stimulators are effective in, for example, providing improvement in procollagen and/or collagen production and/or improvement in maintenance and remodeling of elastin.

Colorants may include, for example, organic and inorganic pigments and pearlescent agents. Suitable inorganic pigments include, but are not limited to, titanium oxide, zirconium oxide, and cerium oxide, as well as zinc oxide, iron oxide, chromium oxide and ferric blue. Suitable organic pigments include barium, strontium, calcium, aluminium lakes and carbon black. Suitable pearlescent agents include mica coated with titanium oxide, iron oxide, or natural pigments.

Various fillers and additional components may be added. Fillers are normally present in an amount of about 0 weight % to about 20 weight %, based on the total weight of the composition, in one embodiment about 0.1 weight % to about 10 weight %. Suitable fillers include without limitation the following: silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

In one embodiment of the invention, the compositions may include additional skin actives such as, but not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, anti-lipid agents, anti-cellulite agents, thiodipropionic acid or esters thereof, and advanced glycation end-product (AGE) inhibitors.

In some embodiments, the cosmetic compositions for combating signs of unwanted subcutaneous fat can further comprise additional anti-lipid agents. For example, the cosmetic composition comprising a Carnitine Palmitoyl Transferase-1 (CPT-1) stimulator (e.g. the leaf extract of *Averrhoa carambola*) in an amount effective (or amounts effective) to improve the appearance of skin may further comprise at least one other anti-lipid agent, including one other anti-cellulite agent. It is contemplated that synergistic improvements may be obtained with such combinations, in some embodiments.

Exemplary anti-cellulite agents include, without limitation, phosphodiesterase inhibitors such as xanthine analogs, caffeine, aminophylline, and theophylline; adenylate cyclase activators, such as forskolin and *Coleus forskohlii* extract; lipolysis stimulators, such as hawthorne extract and cola extract; beta adrenergic receptor agonists such as isoproterenol; alpha-2-adrenergic antagonists such as yohimbine and *Ginkgo biloba* extract; perilla oil (see, e.g., U.S. Pat. No. 7,410,658); carnitine and/or creatine (see, e.g., US 2007/0264205 entitled "Cosmetic Composition having Carnitine Creatinate and Methods for Using," incorporated herein by reference in its entirety).

In a specific embodiment, the composition may comprise at least one additional botanical, such as, for example, a botanical extract, an essential oil, or the plant itself. Suitable botanicals include, without limitation, extracts from *Abies pindrow, Acacia catechu, Anogeissus latifolia, Asmunda japonica, Azadirachta indica, Butea frondosa, Butea monosperma, Cedrus deodara, Emblica officinalis, Ficus benghalensis, Glycyrrhiza glabra, Ilex purpurea* Hassk, *Inula racemosa, Ligusticum chuangxiong, Ligusticum lucidum, Mallotus philippinensis, Mimusops elengi, Morinda citrifolia, Moringa oleifera, Naringi crenulata, Nerium indicum, Psoralea corylifolia, Stenoloma chusana, Terminalia bellerica*, tomato glycolipid and mixtures thereof.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

It is in one embodiment that the composition be essentially free of components having a strong oxidizing potential, including for example, organic or inorganic peroxides. "Essentially free of" these components means that the amounts present are insufficient to have a measurable impact on the activity of an extract of *Serissa japonica*. In some embodiments, this will be, in relation to the amount of *Serissa japonica*, less than 1% by weight.

In one embodiment, the composition of the invention comprising an extract of *Serissa japonica* may have a pH between about 1 and about 8. In certain embodiments, the pH of the composition will be acidic, i.e., less than 7.0, and in one embodiment will be between about 2 and about 7, more in one embodiment between about 3.5 and about 5.5.

Method of Treating Aging or Aged skin

The invention provides a method for treating aging skin by topically applying a composition comprising an extract of *Serissa japonica*, in one embodiment in a cosmetically acceptable vehicle, over the affected area for a period of time sufficient to reduce, ameliorate, reverse or prevent dermatological signs of aging. This method is particularly useful for treating signs of skin photoaging and intrinsic aging.

Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

In one embodiment, the invention provides a method for treating discolored skin by topically applying a composition comprising an extract of *Serissa japonica*, in one embodiment in a cosmetically acceptable vehicle, over the affected area for a period of time sufficient to reduce, ameliorate, reverse or prevent discoloration of the skin. This method is particularly useful for treating discoloration resulting due to photoaging and intrinsic aging. Generally, the improvement in the condition and/or aesthetic appearance of a discoloration of skin is selected from the group consisting of: bleaching hyper-pigmented hair, skin, lips and/or nails; reducing age spots; evening or optimizing skin discoloration; improving the appearance of dark circles under the eyes; treating melasma, cholasma, freckles, after-burn scars, and post-injury hyper-pigmentation; bleaching hair on the scalp, legs, face, and other areas where bleaching and color reduction are desired; reducing melanin production, and/or bleaching nail stains.

In certain embodiments, a composition comprising an extract of *Serissa japonica* may be applied to counter the side effects of various pharmaceuticals know to exacerbate the effects of ageing upon the skin, in particular those known to discolor the skin. These pharmaceuticals include, but are not limited to, antibiotics (sulfonamides and tetracyclines), diuretics, nonsteroidal anti-inflammatory drugs, pain relievers, psychoactive medications, oral contraceptives, antiepileptic agents (hydantoins), chloroquine, DOPA therapy (Levodopa), heavy metals (drugs containing arsenic, bismuth, gold, or silver), and/or chemotherapy agents (cyclophosphamide, 5-fluorouracil, doxorubicin, daunorubicin, and bleomycin). Compositions comprising an extract of *Serissa japonica* may be applied prior to, simultaneously with, or following administration of the pharmaceutical.

The composition will typically be applied to the skin one, two, or three times daily for as long as is necessary to achieve desired anti-aging results. The treatment regimen may comprise daily application for at least one week, at least two weeks, at least four weeks, at least eight weeks, or at least twelve weeks. Chronic treatment regimens are also contemplated.

A composition comprising an extract of *Serissa japonica* is topically applied to an "individual in need thereof," by which is meant an individual that stands to benefits from reducing visible signs of skin damage or aging. In a specific embodiment, the *Serissa japonica* extract is provided in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

In one embodiment, methods for treating fine lines and wrinkles comprise topically applying the inventive compositions comprising a *Serissa japonica* extract to the skin of an individual in need thereof, e.g., topically application directly to the fine line and/or wrinkle in an amount and for a time sufficient to reduce the severity of the fine lines and/or wrinkles or to prevent or inhibit the formation of new fine lines and/or wrinkles. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). This embodiment includes treatment of wrinkles on the skin of the hands, arms, legs, neck, chest, and face, including the forehead.

It is also contemplated that the compositions of the invention will be useful for treating thin skin by topically applying the composition to thin skin of an individual in need thereof. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in patients that have not manifested signs of skin aging, most commonly in individuals under 25 years of age. The method may also reverse or treat signs of aging once manifested as is common in patients over 25 years of age.

EXAMPLES

The following examples describe specific aspects of the invention to illustrate the invention but should not be construed as limiting the invention, as the examples merely provide specific methodology useful in the understanding and practice of the invention and its various aspects.

Example 1

Preparation of *Serissa japonica* Extract

I. Preparation of Purified Plant Extract
Extraction Protocol 1
250 g of dried and powdered material derived from the leaves and stems of *Serissa japonica* was percolated with 1000 ml EtOH/$H_2O$ (50:50, v/v) at room temperature for 24 hours. This percolation was repeated 2 times and then the EtOH/H₂O extraction solution was concentrated under vacuum by rotary evaporator at 40-50° C. to 150 ml or end of distillation, whichever occurs first.

The concentrated solution was then diluted with pure water to 1500 ml of volume and sonicated for 20 minutes to generate an aqueous suspension. The suspension was left to stand at 4° C. for 12 h and then centrifuged. The supernatant was then transferred to a separation funnel where three separate extraction were done with 500 ml of hexane each. The hexane solvent was recycled, and the hexane extract was discarded.

Charcoal (10% by w. vs. total dry matter content) was then added to the aqueous phase yielded from the hexane extraction and stirred for 1 hour. The solution was then filtered and concentrated under vacuum at 40-50° C. to adjust the concentration of solution to 5% (w/v) of its dry matter. The adjusted solution was then passed through a Diaion HP-20 column (20 times of the dry weight,) and washed successively with:

1) H20: 2 times Diaion HP-20 column volume (100 g HP-20 is equal to 210 ml of column volume);

2) 20% aqueous EtOH: 2 times Diaion HP-20 column volume;

3) 50% aqueous EtOH: 2 times Diaion HP-20 column volume;

4) 95% aqueous EtOH: 3 times Diaion HP-20 column volume.

The eluents of washes 1-4 were concentrated, respectively, to dryness to obtain fractions 1-4.

Extraction Protocol 2

Extraction Protocol 2 (Exemplary)

An amount (g) of chopped *Serissa japonica* flowers may be gathered and pulverized. Subsequently, reflux extraction, using methods known to those of ordinary skill in the art, may be conducted using 8-10× the weight of the pulverized flowers of water at 100° C. This step may be repeated. The resulting extract may be filtered and condensed using methods known to those of ordinary skill in the art, after which the extract may undergo vacuum distillation at appropriate conditions known to those of ordinary skill in the art. Subsequently, the extract may be mixed with a suitable amount of dextrin and spray dried.

As noted in the remaining specification, modifications and adaptations of the above-noted extraction process are possible, particularly during a scale-up to larger volumes for production.

II. HPLC The extract of Extraction Protocol I was characterized by high performance liquid chromatography. A sample size of approximately 5 mg/mL was dispersed in 25/75 MeOH/H₂O and sonicated. The characterization was performed on a Zorbax SBC-18 column (7.5 cm×4.6 mm, 3.5 um particle size) and detection was achieved using diode array UV absorbance, 260 nm 300 nm and 360 nm, with lines on FIG. 1 depicted in ascending order and 260 nm on bottom. Operating conditions were flow rate 1.5 ml/min; temperature, 40° C.; sample injection volume, 20 μL, and time of run, 19 minutes. The mobile phase gradient used was as follows. The HPLC characterization of the extract is displayed in FIG. 1. In one embodiment, the extracted composition of the present invention, in substantial isolation, exhibits an HPLC profile substantially similar to that depicted in FIG. 1.

TABLE 1

| Mobile Phase Gradient | |
|---|---|
| Time | Phase |
| 0 Minutes: | 15% Methanol(Solvent B)/85% Water with 1% acetic acid (Solvent A) |
| 10 Minutes: | 95% Methanol/5% Water with 1% Acetic acid. |
| 15 Minutes: | 15% Methanol/85% Water with 1% Acetic acid. |
| 15.01 Minutes | 95% Methanol/5% Water with 1% Acetic acid. |
| 19 Minutes: | 15% Methanol/85% Water with 1% Acetic acid |

Example 2

In Vivo Up-Regulation of Skin Biomarkers

Botanical extracts of *Serissa japonica* were tested for the ability to upregulate skin biomarkers in vivo. 20 healthy female Caucasian subjects aged 30-65 with skin type II or III and mild to moderate photo damage were treated with ingredients on the dorsal forearm for 3 weeks (3 consecutive rounds of 5×24 hour patches under semi-occlusion). Test articles and vehicles were applied in a randomized allocation on five sites on each forearm. Each subject was treated with the extract of *Serissa japonica* at a concentration of 0.2% formulated in Propylene Glycol/Ethanol/H₂O (65:25:10) vehicle and the vehicle control. The application dose was 2 mg/cm². After treatment, a 2 mm punch biopsy was obtained from each treatment site and fixed in 10% buffered formalin. Tissue samples were then embedded in paraffin, sectioned (5 micrometer thickness), processed and stained for the following skin markers—Total Collagen (by Masson Trichrome), Pro-collagen, and Hyaluronic Acid Binding Protein (HABP). In addition, epidermal thickness was evaluated. For each marker, the treated site was compared to the vehicle site to determine the difference in the intensity of the marker. If the intensity of the marker in the treated site is higher relative to control, it indicates improvement of that biomarker. Table 2 shows the percent of subjects that had an improvement in the tested skin biomarkers after three weeks of treatment with an extract of *Serissa japonica*.

TABLE 2

Percent of subjects that had an improvement in the tested skin biomarkers after three weeks of treatment with an extract of *Serissa japonica* (Thumb.)

| Active ingredients | Test rate (% active) | Epidermal Thickening | Total Collagen | pro-Collagen | HABP |
|---|---|---|---|---|---|
| *Serissa japonica* (Thumb.) | 0.200 | 52.8 | 61.1 | 58.3 | 51.4 |

The botanical extract of *Serissa japonica* upregulated several biomarkers, such as epidermal thickening (52.8% of subjects exhibited an increase), collagen (61.1% of subjects exhibited an increase), pro-collagen (58.3% of subjects exhibited an increase), and hyaluronic acid binding protein (51.4% of subjects exhibited an increase), in vivo when topically applied to skin. It is believed that the up-regulation of these biomarkers, which decline in aging skin, leads to an improvement in the appearance of aging or aged skin.

Example 3

Evaluation of Pigment Inhibiting Activity In Vitro

B16 mouse melanoma cells (cell line: ATCC, cat. #: CRL-6475) were grown in DMEM in 96-well tissue culture treated dishes. Cells were exposed to diluted test material or vehicle control for 7 days. Following the treatment period, the level of pigment produced was quantified in the medium using a spectrophotometer at 540 nm. Percent inhibition of pigment production by the test active was calculated relative to vehicle control. *Serissa japonica* (@ 0.01%) inhibited pigment production in the range of about 21-40% relative to the untreated cell cultures (controls).

Example 4

A. Exemplary Anti-Cellulite Compositions

Cosmetic compositions comprising an extract of *Serissa japonica* for topical application to skin exhibiting or at risk of exhibiting hyperpigmentation provided in Table 3.

TABLE 3

| Sample Anti-Cellulite Cosmetic Composition Ingredient |
| --- |
| Aesthetic modifier |
| Emollient |
| Emulsifier |
| Anti-inflammation agent |
| Chelater |
| Coolant |
| Elastin stimulator |
| Exfoliator |
| Fragrance |
| Humectant |
| Microcirculation enhancer |
| Neutralizer |
| Preservative |
| Sunscreen |
| Collagenase/elastinase inhibitor |
| Hawthorne (*Crataeg. monog.*) Fruit. Extract |
| Coffee Seed Extract |
| Soybean (*Glycine soja*) Extract |
| *Celosia cristata* Extract & *Prunella vulgaris* Extract |
| L-Carnitine Hydrochloride |
| *Averrhoa carambola* Leaf Extract |
| *Serissa japonica* extract |
| Demineralized water |

B. Exemplary Anti-Aging Compositions

Cosmetic compositions comprising an extract of *Serissa japonica* for topical application to skin exhibiting signs of aging or aged skin are provided in Table 4.

TABLE 4

| Sample Anti-Aging Facial Cosmetic Composition Ingredient |
| --- |
| Aesthetic modifier |
| Emollient |
| Emulsifier |
| Anti-inflammation agent |
| Chelater |
| Coolant |
| Elastin stimulator |
| Exfoliator |
| Fragrance |
| Humectant |
| Microcirculation enhancer |
| Neutralizer |
| Preservative |
| Sunscreen |
| Collagenase/elastinase inhibitor |
| Phytol |
| Antioxidant |

TABLE 4-continued

| Sample Anti-Aging Facial Cosmetic Composition Ingredient |
| --- |
| Fennel Extract |
| Carrot extract |
| Pomegranate extract |
| Thiodipropionic acid (TDPA) |
| Green tea polyphenol |
| L-4 Thiazolylanine |
| *Serissa japonica* extract |
| Demineralized water |

C. Exemplary Skin Lightening Compositions

Cosmetic compositions comprising an extract of *Callistephus chinensis* for topical application to skin exhibiting signs of hyperpigmentation are provided in Table 5.

TABLE 5

| Sample Skin Lightening Compositions Description |
| --- |
| Demineralized Water |
| Carbopol 934 |
| Acrylates/C10-30 Alkyl Acrylate Crosspolymer |
| Acrylates/C10-30 Alkyl Acrylate Crosspolymer |
| Xanthan Gum |
| Disodium EDTA - Tech Grade |
| Methylparaben |
| Alcohol SD40B |
| Alcohol Mixture (3210&1901 92.52-7.48) |
| Alcohol Mixture (3215&1901 92.52-7.48) |
| Phenoxyethanol-98% MIN (*RI*) |
| Butylene Glycol |
| Pentylene Glycol (*RI*) |
| Ethoxydiglycol |
| ISODODECANE |
| Dilauryl Thiodipropionate |
| Tetrahexyldecyl Ascorbate |
| Ascorbyl Glucoside |
| Glycyrrhizinate - Dipotassium Unp. |
| Silica Shells |
| Sodium Hydroxide Solution 50% |
| Silicone Fluid SF-96-5 |
| PEG-40 Stearate |
| Steareth-2 |
| *Saxifraga Sarmentosa*/Grape Extract |
| *Saccharomyces*/Zinc ferment |
| Yeast Extract |
| Kudzu (*Pueraria Lobata*) Symbiosome extract |
| Soybean (*Gly. Soja*) Extract |
| Carrot (*Daucus Carota Sativa*) Root Extract |
| Phytol |
| Dimethicone/Dimethicone Crosspolymer |
| Thiodipropionic Acid |
| *S. Japonica* Extract |

These compositions, the above-noted anti-cellulite, anti-aging and skin lightening cosmetic compositions, are believed to be effective to treat, reverse, ameliorate and/or prevent signs of cellulite, aging, and/or hyperpigmentation, specifically, the compositions are believed to reduce the appearance of cellulite, wrinkles, lines, and sagging in the skin, and discoloration of the skin, respectively. The compositions of Tables 3-5 are applied to skin in need of treatment, by which is meant skin in need of an anti-cellulite, anti-aging, or skin lightening benefit, respectively. The cosmetic compositions may be applied directly to the skin in need of treatment.

These cosmetic compositions are applied to aged or discolored skin, two or three times daily for as long as is necessary to achieve desired anti-aging or skin lightening results, a treatment regimen which may comprise daily application for at least one week, at least two weeks, at least four weeks, at least eight weeks, or at least twelve weeks. Alternatively, the exemplary cosmetic compositions may be used in chronic treatment of aged or discolored skin.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:

1. A method of thickening the epidermis of skin in individuals having thinning skin, comprising topically applying to the thinning skin a composition comprising, in a cosmetically acceptable vehicle, an extract of *Serissa japonica* in an amount effective to thicken said thinning skin, wherein said extract is an ethanol:water extract derived from leaves and stems of *Serissa japonica*.

2. The method according to claim 1, wherein the composition is topically applied at least once daily for at least one week.

3. The method according to claim 1, wherein the extract is present in an amount about 0.0001 wt % to about 90 wt % based on the total weight of the composition.

4. The method according to claim 3, wherein the extract is present in an amount of from about 0.01 wt % to about 10 wt % of the total weight of the composition.

5. The method of claim 1, wherein the composition is in an aerosol spray, cream, emulsion, solid, liquid, dispersion, foam, gel, lotion, mousse, ointment, powder, patch, pomade, solution, pump spray, stick or towelette.

* * * * *